United States Patent [19]

O'Connor et al.

[11] Patent Number: 4,928,532
[45] Date of Patent: May 29, 1990

[54] HYDROSTATIC SELF-ALIGNING AXIAL/TORSIONAL MECHANISM

[75] Inventors: Daniel G. O'Connor; Howard L. Gerth, both of Knoxville, Tenn.

[73] Assignee: The United States of America as represented by the United States Department of Energy, Washington, D.C.

[21] Appl. No.: 355,585

[22] Filed: May 23, 1989

[51] Int. Cl.⁵ .............................................. G01N 3/02
[52] U.S. Cl. ........................................ 73/856; 73/837
[58] Field of Search ................ 73/794, 856, 826, 831, 73/834, 837, 847; 403/57, 58

[56] References Cited

U.S. PATENT DOCUMENTS 4,686,860  8/1987  Liu .......................................... 73/856
4,843,888  7/1989  Gram et al. ............................ 73/856

Primary Examiner—Jerry W. Myracle
Attorney, Agent, or Firm—Stephen D. Hamel; William R. Moser; Richard E. Constant

[57] ABSTRACT

The present invention is directed to a self-aligning axial/torsional loading mechanism for testing the strength of brittle materials which are sensitive to bending moments. Disposed inside said self-aligning loading mechanism is a frictionless hydrostatic ball joint with a flexure ring to accommodate torsional loads through said ball joint.

2 Claims, 2 Drawing Sheets

4,928,532

HYDROSTATIC SELF-ALIGNING AXIAL/TORSIONAL MECHANISM

This invention was made as a result of work done under contract DE-AC05-84OR21400 between Martin Marietta Energy Systems, Inc., and the United States Department of Energy.

BACKGROUND OF THE INVENTION

The present invention relates generally to a hydrostatic self-aligning loading mechanism for applying a controlled axial and/or torsional load to a test specimen without introducing bending moments induced by conventional testing means.

Recent developments in carbon-carbon composites and ceramics have substantially advanced the state of the art and have resulted in the development of interest in such materials for use in structural applications.

Currently, there is no way to test these materials in a multiaxial stress state without imparting some undesirable stresses to the materials being tested due to alignment problems in the apparatus loading the test specimen.

Considerable effort has been made in an attempt to satisfy a long-felt need for determining properties of brittle materials such as carbon-carbon composites and ceramics. Most efforts have focused on compressive, torsional, and tensile tests. A need exists for expanding capabilities to include multiaxial testing. Because brittle materials are extremely sensitive to misalignment during testing, it has not been possible to test these types of materails biaxially, that is, in a combined axial-torsional mode. These types of tests are imperative, however, for developing design guidelines for structural applications of brittle materials. Accordingly, a means is needed that will maintain alignment of a brittle test specimen continually during a test involving combined axial-torsional loading.

One device which provides an alignment function is a universal joint. However, a universal joint has too much play in the bearings and imposes significant bending moments on the specimen. If the bearings are replaced by flexures, the universal joint does not have the necessary load carrying capacity.

U.S. Pat. No. 4,686,860 describes a device which allows only axial testing. In this invention a multiplicity of hydraulic piston assemblies are equally spaced in a hydraulic housing assembly on a circle about the centerline of the tensile specimen; the hydraulic piston assemblies being interconnected by oil channels that are a part of an oil distribution manifold. A pull rod assembly is provided with a circular flange which rests on the top of the piston assemblies and a pull rod which extends downwardly through the center hold of the housing assembly for gripping the pull rod end of a ceramic specimen.

Use of a hydraulic fluid as a distribution medium to divide the applied load into a multiplicity of equal parts counteracted by the circular array of miniature pistons is a key feature of this invention. The seals used in this device cause some amount of friction which imposes an undesirable bending movement in a specimen.

It is accordingly a general object of this invention to provide a means for accurately testing the tensile strength of brittle specimens.

it is also an object of this invention to provide a means for aligning ceramic grippers.

Another more particular object of the invention is to provide a means for applying biaxial stress to a specimen without inducing significant bending moments in the specimen.

SUMMARY OF THE INVENTION

In accordance with the invention, a hydrostatic, self-aligning, axial/torsional loading mechanism is provided for use in testing the strength of brittle specimens. The loading mechanism consists of two major components: a frictionless ball joint assembly and a flexure ring. A ball stud, with the ball portion being a spherical bearing is adapted to accept a flexure ring disposed about the center of the ball portion on a plane perpendicular to the center line of the ball stud. The flexure ring, having a thickened portion, is rigidly affixed to a flat surface about the equator of the ball portion of the ball stud. Stud portion of the ball stud is adapted for attaching to a load or gripping means, said adaptation preferably comprising machine threads.

A split housing, comprising in relation to the load, a distal half and a proximal half supports said ball stud and flexure ring assembly. The distal half is adapted at the end opposite the proximal half to retrofit existing equipment, while the proximal half, at the end opposite the distal half has an opening through which the ball stud protrudes. Inner surfaces of each half (distal and proximal) support the ball stud in accordance of known hydrostatic spherical bearing technology, clearance is also provided for the thickened portion of the flexure ring. Recesses equally spaced in the distal and proximal portions carry hydraulic fluid from pressurized supply ports to bearing surfaces on the ball stud. Return ports located in both the distal and proximal portions allow the hydraulic fluid to be recycled to the pressuring means. A flexible boot is sealably disposed around the stud portion of the ball stud and sealed to the proximal housing to retain hydrualic fluid that may travel through the opening through which the ball stud protrudes.

The subject invention operates by allowing the ball stud to align so that all imposed tensional or pressure forces are transmitted through the center line of the stud portion. Use of the flexure ring imparts no friction upon the ball joint, only a spring constant which is negligible. Movement of the ball stud is essentially frictionless in the aligning mode. Therefore, the stud portion may move freely in "joy stick" fashion, however, the flexure ring serving its intended purpose, prevents torsional or twisting movement of the ball stud. Thus, all torsional forces imposed on the housing are transmitted through the flexure ring and to the ball stud.

When two devices are positioned opposingly and "roughly" aligned by conventional aligning means a specimen may be placed and gripped between the devices and accurately tested for axial strength, torsonal strength, or a combination of the two, this is accomplished with a minimal and negligible amount of bending being imposed upon the specimen.

Use of a hydrostatic bearing in a loading train is unique in itself. Addition of the flexure ring to provide strength yet flexibility is a key feature of the invention.

Other and further objects of the invention will be obvious upon an examination of the illustrative embodiment (or method) about to be described or will be indicated in the appended claims, and various advantages not referred to herein will occur to those skilled in the art upon employment of the invention in practice.

DETAILED DESCRIPTION OF THE INVENTION

As briefly mentioned above, the present invention is directed to providing a hydrostatic, self-aligning, axial/torsional loading mechanism comprising an essentially frictionless ball joint with a flexure ring disposed around the center of the ball so as to transmit torsional force through said ball joint.

Figure 1:
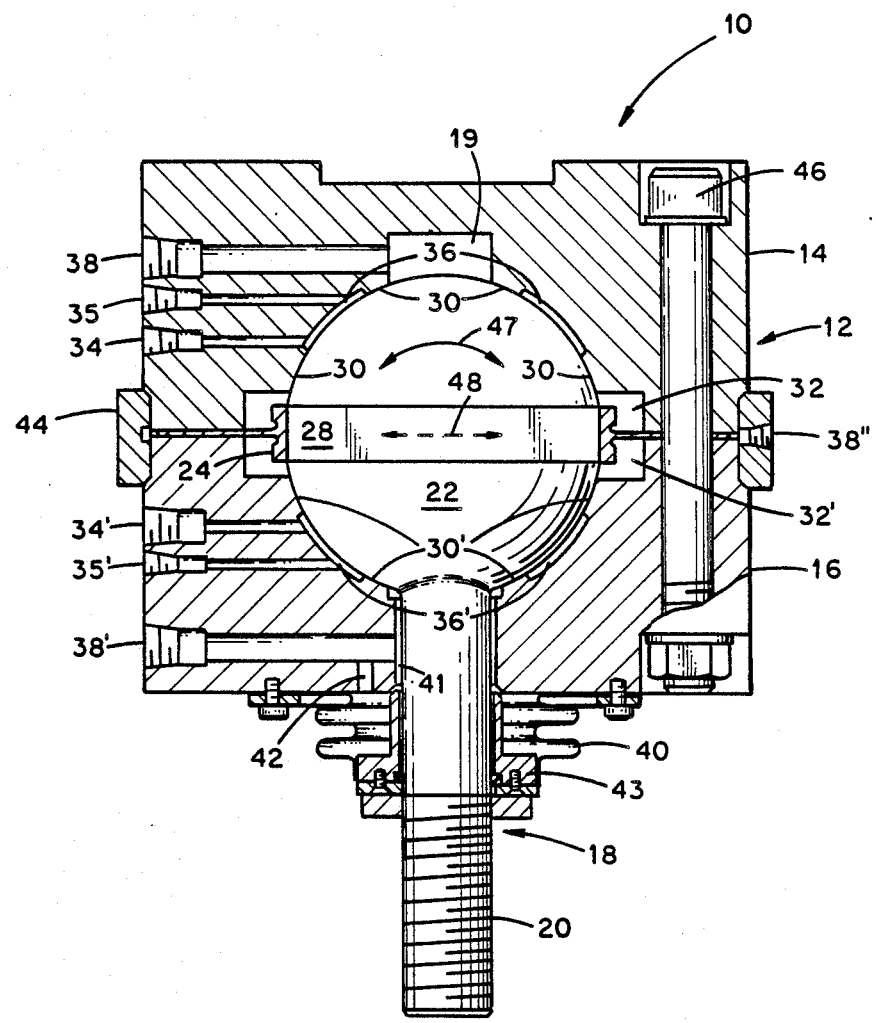
FIG. 1 is a cross sectional view of the hydrostatic, self-aligning, axial/torsional loading mechanism in accordance with the present invention.

Described in general detail and with reference to the accompanying drawings, the hydrostatic, self-aligning loading mechanism assembly is shown at 10 in FIG. 1. Hydrostatic, self-aligning loading mechanism assembly 10 includes a split housing assembly 12 comprising a distal half 14 and proximal half 16 which accommodates ball stud assembly 18.

Ball stud assembly 18 consists of ball stud 20 and ball portion 22 which is a spherical bearing, that is adapted to accept a flexure ring 24 around the center of the ball portion 22 on a plane perpendicular to the center line of the ball stud 20. Flexure ring 24, having a thickened portion is rigidly affixed to flat 28 on the equator of ball portion 22 of the ball stud assembly 18. Stud portion 20 of ball stud assembly 18 is adapted to attach to a load or load gripping means, said adaptation preferably comprising machined threads.

Split housing 12 comprised of distal half 14 and proximal half 16, accommodating ball stud assembly 18 and flexure ring 24 is adapted to retrofit hydraulic lines. Distal half 14 has an opening 19 for pressure balancing. The inner surfaces of distal half 14 and proximal half 16, 30 and 30' support ball stud assembly 18 in known hydrostatic spherical bearing technology. Clearance for flexure ring 24 in provided by annular grooves 32 and 32' in distal half 14 and proximal half 16. Pressurized hydraulic fluid enters through ports 34-34' into annular grooves 36-36' of distal half 14 and proximal half 16 to bearing surfaces 30-30'. Ports 35-35' are for pressure sensing. Return ports 38-38'-38" allow the hydraulic fluid to return to the pressurizing means. A thin rubber bellows 40, attached by conventional means is sealably disposed around stud portion 20 and sealed to the distal half 16, to retain hydraulic fluid that may flow through the clearance of opening 41 through which ball stud 20 protrudes. Opening 42 provides a means for draining fluid from boot 40. Split housing assembly 12, consisting of distal half 14 and proximal half 16 clamp and hold securely flexure ring 24. The distal and proximal halfs (14 and 16) are aligned by alignment ring 44 and secured by bolts 46.

Figure 2:
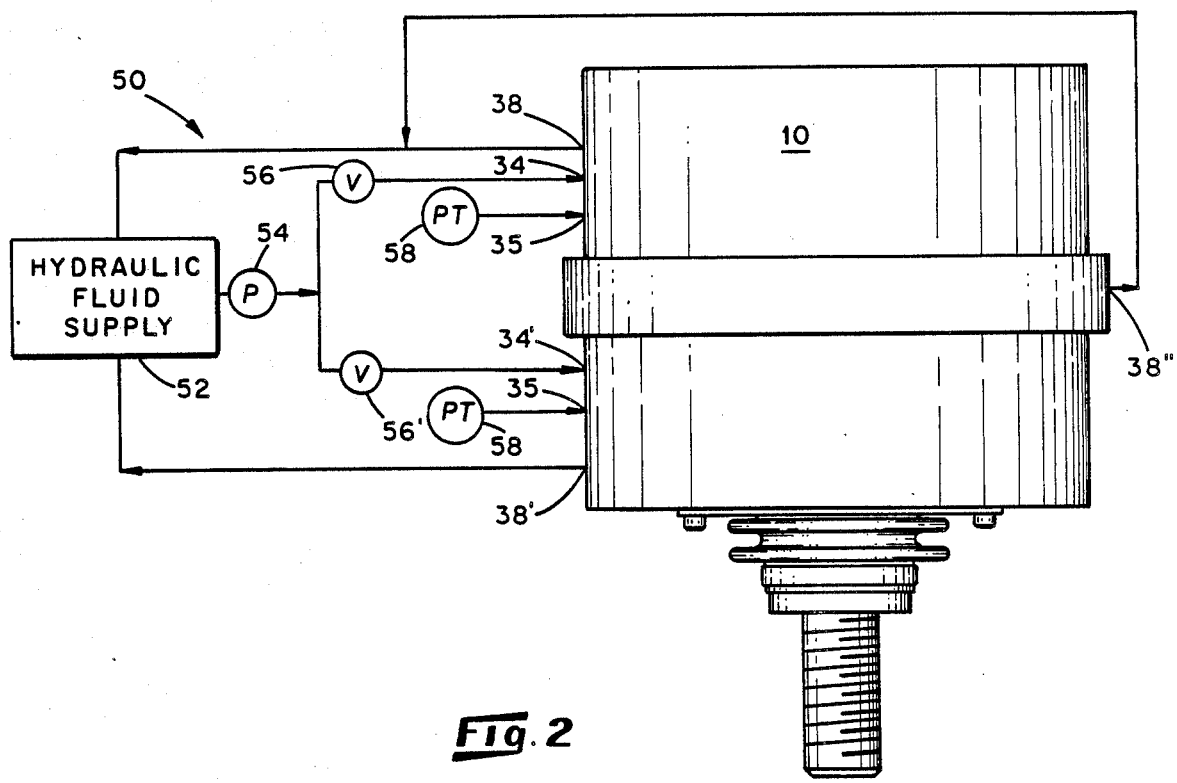
FIG. 2 is an assembled view of the hydrostatic, self-aligning axial/torsional loading mechanism with the attendant hydrualic support system.

Referring now to FIG. 2, hydrostatic loading mechanism 10 is integral with hydraulic system 50. Hydraulic fluid supply source 52 supplies fluid through pump 54 to control valves 56-56' into pressure transducers 58-58'. The hydraulic fluid then enters as the hydrostatic loading mechanism assembly 10 through supply ports 34-34' into cavities 36-36' (FIG. 1) exiting through return ports 38-38'-38" returning to hydraulic fluid supply source 52.

In operation ball stud 20 is designed for less than one degree of rotation about the center of ball 22 because flex ring 24 will experience very high stresses if the ball stud is allowed to rotate very much. Very little rotation is actually required to maintain alignment of ball stud 20, therefore, prohibiting high stresses in flexure ring 24. Care is taken when assembling loading mechanism assembly 10 or when moving said mechanism not to over stress flexure ring 24. Retaining sleeve 43 prohibits ball stud 20 from swinging free between tests by engaging it against proximal housing 16.

In operation ball stud assembly 18 is aligned so that all imposed tensional or pressure forces are transmitted through the center line of stud portion 20. Flexure ring 24 imparts no friction on ball joint assembly 18, only a spring constant which is negligible. Movement of ball 2 is essentially frictionless in the aligning mode. Therefore, stud portion 20 may move freely in "joy stick" fashion as shown by arrows 47. Then flexure ring 24, serving its intended purpose, prevents torsional or twisting movement of ball stud assembly 18 as shown by dashed arrows 48. Therefore, all torsional forces imposed on split housing assembly 12 are transmitted through the flexure ring 24 and ball stud assembly 18.

When two hydrostatic self-aligning loading mechanism assemblies 10, are opposingly positioned and "roughly" aligned by conventional aligning means, a specimen may be placed and gripped between said device and thus accurately tested for axial strength, torsional strength, or a combination of the two, this is with a minimal and megligible amount of bending moment being imposed upon the specimen.

The hydrostatic self-aligning loading mechanism 10 is designed for use in structural testing as opposed to a production facility that turns out many data points for a particular material characteristics, although it may be utilized in such a capacity. Flexure ring 24 allows less than 4 inch-pounds bending moment on a specimen.

In operation the hydraulic supply 52 is sized to meet the specific pressure requirement dictated by the testing load. By geometrically modifying the hydraulic loading mechanism, the area available on ball 22 and split housing assembly 12 may be varied to carry anticipated loads. The pressure at the recesses 36-36' should be about half the supply pressure so that the mechanism as a whole is responsive to fluctuating loads during a test. The pressures at recesses 36-36' may be measured and controlled by valves 56-56' and pressure transducers 58-58' to fine tune with hydrostatic loading mechanism 10. Hydrostatic loading mechanism 10 was designed to withstand an internal pressure of 10,000 psi with the presently known materials and assembly procedures. Ball stud 20 was designed for an axial load of 50,000 pounds and a maximum combined torsonal load of 25,000 inch-pounds.

The above description of a preferred embodiment of the invention should not be interpreted in a limiting sense. For example, the size of the hydrostatic loading mechanism can be varied to provide different loading requirements as long as the axial alignment is accomplished by a spherical, essentially frictionless bearing, and the torsional strength is provided by a thin continuous flat flex ring located about the equator of the sphere. A fluid must be pumped through the bearing to accomplish the requirement that demands no significant bending loads. It would be possible to use a spherical roller bearing with the same flexure ring is a particular application does not require such restriction of bending loads. Also, it would be possible to use a spherical roller bearing with the same flexure ring without department from the scope of the invention. It is intended rather than the invention be limited only by the claims appended hereto.

We claim:

1. A self-aligning loading mechanism for applying a controlled axial and/or torsional load to a test specimen comprising:
    (a) a split support housing having a distal half and a proximal half defining a spherical cavity; said proximal half, having an opening from said spherical cavity;
    (b) annular recesses equally spaced within said support housing about said spherical cavity;
    (c) an essentially frictionless ball stud, the ball portion of said ball stud being a spherical bearing, and having a flat surface about the equator of said ball portion of said ball stud.
    (d) a flexure ring having a thickened portion, rigidly affixed to said flat portion about the equator of said ball portion of said ball stud;
    (e) a means for supplying pressurized oil to each of said annular recesses at the same oil pressure;
    (f) a stud portion of said ball stud extending through said opening in said proximal half support housing; and said stud portion of said ball stud being adapted to attach a load or gripping means.

2. The self-aligning loading mechanism for claim 1 wherein said means for supplying pressurized oil to each of said annular recesses comprises a multiplicity of pressurized ports in said split housing, said pressurized ports carrying hydraulic fluid from said means for supplying pressurized oil to said annular recesses.

* * * * *